US008455552B2

(12) United States Patent
Savion et al.

(10) Patent No.: US 8,455,552 B2
(45) Date of Patent: Jun. 4, 2013

(54) COMPOSITION COMPRISING
S-ALLYLMERCAPTO-N-ACETYLCYSTEINE
(ASSNAC) FOR UP-REGULATION OF
CELLULAR GLUTATHIONE LEVEL

(75) Inventors: Naphtali Savion, Givat Shmuel (IL);
David Mirelman, Ramat Efal (IL);
Aharon Rabinkov, Rehovot (IL); Alex Khenkin, Rehovot (IL)

(73) Assignees: RAMOT et Tel Aviv University Ltd.,
Tel Aviv (IL); Yeda Research and Development Co. Ltd., Rehovot (IL)

( * ) Notice: Subject to any disclaimer, the term of this patent is extended or adjusted under 35 U.S.C. 154(b) by 637 days.

(21) Appl. No.: 12/597,956

(22) PCT Filed: May 1, 2008

(86) PCT No.: PCT/IL2008/000600
§ 371 (c)(1),
(2), (4) Date: Dec. 9, 2009

(87) PCT Pub. No.: WO2008/135984
PCT Pub. Date: Nov. 13, 2008

(65) Prior Publication Data
US 2011/0178152 A1 Jul. 21, 2011

Related U.S. Application Data

(60) Provisional application No. 60/915,741, filed on May 3, 2007.

(51) Int. Cl.
*A01N 41/12* (2006.01)
*A61K 31/105* (2006.01)
*C07C 321/00* (2006.01)
*C07C 323/00* (2006.01)
*C07C 381/00* (2006.01)

(52) U.S. Cl.
USPC .................................. 514/707; 568/21

(58) Field of Classification Search
USPC .................................. 514/707; 568/21
See application file for complete search history.

(56) References Cited

U.S. PATENT DOCUMENTS

| 3,892,852 | A | | 7/1975 | Joullie et al. | |
| 5,380,747 | A | * | 1/1995 | Medford et al. | ............. 514/423 |

FOREIGN PATENT DOCUMENTS

| DE | 4325547 A1 | * | 2/1995 |
| EP | 0885608 B2 | | 12/1998 |
| JP | 62063517 B2 | | 3/1987 |
| JP | 07013011 | * | 2/1995 |
| WO | 2005/017094 A1 | | 2/2005 |

OTHER PUBLICATIONS

Kominato et. al., JP 07-013011, CAS STN abstract.*
Stehbens, Experimental and Molecular Pathology, 2004, Elsevier, vol. 77, pp. 121-132.*
http://www.thefreedictionary.com/prevent.*
http://www.cancer.gov/cancertopics/types/alphalist/y.*
http://info.cancerresearchuk.org/healthyliving/introducingcancerprevention/.*
Cuzick et. al., The Lancet, 2003, The Lancet Publishing Group, vol. 361, pp. 296-300.*
Surh, Nature Rev. Cancer, 2003, Nature Publishing Group, vol. 3, pp. 768-780.*
Chong et. al., Brain Res. Brain Res. Rev., 2005, National Institutes of Health, vol. 49, No. 1, pp. 1-21.*
Dauer et. al., Neuron, 2003, Cell Press, vol. 39, pp. 889-909.*
Grumelli et. al., PLOS Medicine, 2004, PLOS Medicine Org., vol. 1, issue 1, pp. 075-083.*
Chabner et. al., Nature Reviews Cancer, 2005, Nature Publishing Group, vol. 5, pp. 65-72.*
Leaf, Fortune, Mar. 2004, Time Inc., pp. 1-13.*
Kearns et. al., Blood, 2001, American Society of Hematology, vol. 97, pp. 393-398.*
Wilson, The International Journal of Biochemistry and Cell Biology, 2004, Elsevier, vol. 36, pp. 1868-1873.*
Weishaupt et. al., Journal of Pineal Research, 2006, Blackwell Munksgaard, vol. 41, pp. 313-323.*
Singh et. al., Pathophysiology, 2006, Elsevier, vol. 13, pp. 129-142.*
Jenner, Annals of Neurology, 2003, Wiley-Liss Inc., vol. 53, supplemental 3, pp. S26-S38.*
Database CA (online) Chemical abstracts service, Columbus, Ohio, us; Jul. 25, 1987, Kominato, Jo et al., Pharmaceuticals containing cysteine derivatives for treatment of liver disease XP0024994822 retrieved from STN Database accession No. 1987:428398 abstract and JP 62063517 Riken chemical industry Co., Ltd., Japan Mar. 20, 1987.
Database WPI Week 198717 Thomson Scientific, London, GB; AN 1987-119466 XP002494952 and JP 62063517, Jul. 1987.
Anderson, M. E., "Glutathione: an overview of biosynthesis and modulation", Chem. Biol. Interact, 112:1-14 (1998).
Bergamini, C. M. et al., "Oxygen, reactive oxygen species and tissue damage", Curr. Pharm. Des, 10:1611-1626 (2004).
Berge, Stephen M. et al., "Pharmaceutical salts", J. Pharm. Sci., 66:1-19 (1977).

(Continued)

*Primary Examiner* — Sreeni Padmanabhan
*Assistant Examiner* — Sarah Pihonak
(74) *Attorney, Agent, or Firm* — Rodney J. Fuller; Booth Udall Fuller, PLC

(57) ABSTRACT

The present invention relates to S-allylmercapto-N-acetylcysteine (ASSNAC) and its pharmaceutically acceptable salts and solvates, which are useful for up-regulation of cellular glutathione levels and expression of phase II detoxifying enzymes. The invention further provides methods of use thereof in the prevention, alleviation or treatment of oxidative stress induced by reactive oxygen species (ROS).

25 Claims, 9 Drawing Sheets

OTHER PUBLICATIONS

Brown, Nicholas S. et al., "Hypoxia and oxidative stress in breast cancer Oxidative Stress: its effects on growth, metastatic potential and response to therapy of breast cancer", Breast Cancer Res, 3:323-327 (2001).

Dickinson, D. A. et al., "Glutathione in defense and signaling—Lessons from a small thiol", Ann. N. Y. Acad. Sci, 973:488-504 (2002).

Horev-Azaria, L. et al., "Allicin Up-Regulates Cellular Glutathione Level in Vascular Endothelial Cells", Eur J. Nature, 48:67-74 (2009).

Kevil, C. G. et al., "Regulation of endothelial glutathione by ICAM-1: implications for inflammation", FASEB J, 18:1321-1323 (2004).

Kim, C. H. et al., "Pyrrolidine Dithiocarbamate Induces Bovine Cerebral Endothelial Cell Death by Increasing the Intracellular Zinc Level", J. Neurochem., 72:1586-1592 (1999).

Lawson, Larry D., "Garlic: a review of its medicinal effects and indicated active compounds" in: Lawson, Larry D. and Bauer, Rudolf (Eds.), Phytomedicines of Europe: Their Chemistry and Biological Activity, American Chemical Society, Washington, DC pp. 176-209 (1998).

Liu, H. et al., "Glutathione metabolism during aging and in Alzheimer disease", Ann. N. Y. Acad. Sci., 1019:346-349 (2004).

Masella, R. et al., "Novel mechanisms of natural antioxidant compounds in biological systems: involvement of glutathione and glutathione-related enzymes" J. Nutr. Biochem., 16:577-586 (2005).

Miron, T. et al., "The mode of action of allicin: its ready permeability through phospholipid membranes may contribute to its biological activity", Biochim. Biophys. Acta, 1463:20-30 (2000).

Oliviera, H. C. F. et al., "Oxidative stress in atherosclerosis-prone mouse is due to low antioxidant capacity of mitochondria", FASEB J, 19:278-280 (2005).

Rabinkov, A. et al., "The mode of action of allicin: trapping of radicals and interaction with thiol containing proteins", Biochim. Biophys. Acta, 1379:233-244 (1998).

Sies, H., "Role of reactive oxygen species in biological processes", Klin Wochenschr, 69: 965-968 (1991).

Thomson, Martha. et al., "Garlic (*Allium sativum*): a review of its potential use as an anticancer agent", Curr cancer drug targets, 3:67-81(2003).

* cited by examiner

COMPOSITION COMPRISING S-ALLYLMERCAPTO-N-ACETYLCYSTEINE (ASSNAC) FOR UP-REGULATION OF CELLULAR GLUTATHIONE LEVEL

RELATED APPLICATION DATA

This application is the U.S. national stage of PCT/IL2008/000600 filed May 1, 2008, which claims the benefit of U.S. Provisional Application No. 60/915,741, filed May 3, 2007, the contents of each of which are herein incorporated by reference for all purposes.

FIELD OF INVENTION

The present invention relates to compositions that are useful for up-regulation of cellular glutathione levels and for the prevention, alleviation or treatment of oxidative stress induced by reactive oxygen species.

BACKGROUND OF THE INVENTION

Reactive oxygen species (ROS) can cause major damage to cells by oxidizing lipids, proteins, carbohydrates and DNA in cells and tissues. This undesirable oxidation results in membrane damage, protein modification and DNA impairment that can give rise to death of cells and tissues. ROS induced oxidative stress is associated with pathological diseases like atherosclerosis (Oliviera et al., *FASEB J.* 19, 278, 2005; Kevil, *FASEB J.* 18, 1321, 2004), diabetes type 2, neurodegenerative diseases (Bergamini, *Curr. Pharm. Des.* 10, 1611, 2004; Masella, *J. Nutr. Biochem.* 16, 577, 2005) and cancer (Brown, *Breast Cancer Res.* 3, 323, 2001).

Glutathione is the major cellular anti-oxidant. Under normal conditions, 99% of the total glutathione is in the form of reduced glutathione, GSH. Protection against ROS is obtained by forming oxidized glutathione (GSSG) or other GSH conjugates (Bergamini, *Curr. Pharm. Des.* 10, 1611, 2004). The formed GSSG can be enzymatically reduced by glutathione reductase or alternatively excreted out of the cell to maintain the high cellular GSH/GSSG ratio (Dickinson, *Ann. N.Y. Acad. Sci.* 973, 488, 2002). Glutathione is thus highly important for cellular function, wherein imbalance in cellular GSH/GSSG ratio is associated with various pathological processes such as arthritis, atherosclerosis, type 2 diabetes, cancer and neurodegenerative diseases such as Alzheimer's disease and Parkinson's disease (Liu, *Ann. N.Y. Acad. Sci.* 1019, 346, 2004). It is therefore highly important to find means for up-regulating cellular glutathione level.

GSH synthesis in cells is normally regulated by feedback inhibition of the rate-limiting enzyme glutamate-cysteine-ligase (Anderson, *Chem. Biol. Interact.* 112, 1, 1998). Cysteine is known as a precursor for glutathione biosynthesis and its concentration controls the rate of glutathione biosynthesis.

N-acetylcysteine (NAC) is used as a food supplement aimed to supply cells with cysteine thereby increasing glutathione cellular level. However, NAC penetration to the brain and other tissues is limited. Pyrrolidine dithiocarbamate (PDTC) is known to have antioxidant properties and is considered as a potential NF-κB inhibitor (Kim et al., *J. Neurochem.* 72, 1586, 1999).

Allicin, the garlic primary active compound, is a small molecule that freely permeates through phospholipids bilayers. The allicin molecule interacts with different thiol containing compounds via the thiol functional groups to form various metabolites containing disulfide bonds, such as S-allylmercaptoglutathione (GSSA) or S-allylmercaptocysteine (CSSA) (Lawson in *Phytomedicines of Europe: Their Chemistry and Biological Activity*, A.C.S., Washington D. C., 176, 1998; Miron, *Biochim. Biophys. Acta* 1463, 20, 2000).

Japanese patent No. 62063517 discloses pharmaceutical compositions of cysteine derivatives for the treatment of liver diseases. Amongst the derivatives disclosed in JP-62063517 is S-allylmercapto-N-acetylcysteine (ASSNAC).

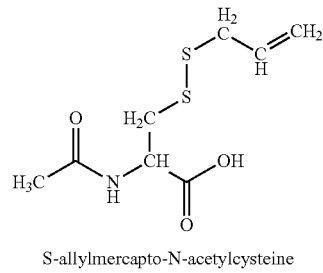

S-allylmercapto-N-acetylcysteine

There is an unmet need for effective and safe prevention and treatment of oxidative stress in vivo. Furthermore, there is an unmet need for readily bioavailable and non-toxic agents to elevate the natural body levels of anti-oxidant glutathione.

SUMMARY OF THE INVENTION

The present invention discloses that compositions comprising S-allymercapto-N-acetylcysteine (ASSNAC) and its salts and solvates, are useful for the prevention, alleviation and treatment of the detrimental effects of oxidative stress caused by reactive oxygen species (ROS). The compositions disclosed herein are surprisingly superior to S-allylmercaptocysteine and N-acetylcysteine. Within the scope of the present invention are pharmaceutical compositions comprising ASSNAC and its pharmaceutically acceptable salts and solvates for preventing, alleviating and treating pathological conditions and diseases characterized by increased induction of oxidative stress. Specifically, these compositions up-regulate cellular glutathione levels particularly within cells of the central nervous system (CNS). Further disclosed are compositions comprising ASSNAC and pyrrolidine dithiocarbamate (PDTC) for preventing, alleviating and treating ROS-related oxidative stress.

According to one aspect, the present invention provides compositions and methods for up-regulating cellular glutathione levels, comprising the step of administering an effective amount of a pharmaceutical composition comprising as an active ingredient ASSNAC and pharmaceutically acceptable salts and solvates thereof. According to some embodiments, the present invention provides compositions and methods for up-regulating cellular glutathione levels in cells of the central nervous system (CNS).

According to another aspect the present invention provides methods for up-regulating cellular glutathione levels, comprising the step of administering an effective amount of a pharmaceutical composition comprising as an active ingredient ASSNAC and pharmaceutically acceptable salts and solvates thereof, and further comprising co-administering a pharmaceutically effective amount of at least one other active agent. In one embodiment, the at least one active agent is pyrrolidine dithiocarbamate (PDTC).

In certain embodiments, the present invention provides methods for preventing, alleviating or treating oxidative stress induced by ROS, comprising the step of administering an effective amount of a pharmaceutical composition comprising as an active ingredient ASSNAC and pharmaceutically acceptable salts and solvates thereof.

According to other embodiments, the methods for preventing, alleviating or treating oxidative stress induced by ROS are useful for disorders in the central nervous system.

According to some embodiments, the present invention provides a method of preventing, alleviating or treating ROS-related oxidative stress resulting from, but not limited to, an oxidizing agent, increased oxygen exposure, oxygen-induced degeneration or disease, reperfusion injury, ionizing radiation, carcinogenic agents, chemotherapeutic agents, mutagenic agents and laser irradiation damages. According to other embodiments, the method disclosed herein is useful for preventing, alleviating or treating ROS-related oxidative stress in the CNS.

According to another aspect, the present invention relates to the prevention, alleviation or treatment of oxidative stress induced by ROS, comprising the step of administering an effective amount of a pharmaceutical composition comprising as an active ingredient ASSNAC or pharmaceutically acceptable salts and solvates thereof, and further comprising co-administering an effective amount of at least one other active agent. In some embodiments, the at least one other active agent is pyrrolidine dithiocarbamate (PDTC).

According to another aspect, the present invention relates to the use of ASSNAC and pharmaceutically acceptable salts and solvates thereof for the preparation of a medicament for the up-regulation of cellular glutathione levels. In a currently preferred embodiment, the medicament according to the present invention is useful for up-regulating cellular glutathione levels in cells that are part of the central nervous system.

According to another aspect, the present invention relates to the use of ASSNAC and pharmaceutically acceptable salts and solvates thereof for the preparation of a medicament for preventing, alleviating or treating oxidative stress induced by ROS. In one embodiment, the medicament for preventing, alleviating or treating oxidative stress induced by ROS is designated for cells that are part of the central nervous system.

In yet another aspect, the present invention provides the use of a pharmaceutical composition comprising as an active ingredient ASSNAC and pharmaceutically acceptable salts and solvates thereof for the preparation of a medicament for preventing, alleviating or treating oxidative stress induced by ROS, in combination therapy with at least one other active agent, for improving the effectiveness of the prevention, alleviation or treatment. In a currently preferred embodiment, the second active agent is pyrrolidine dithiocarbamate (PDTC).

According to another aspect, the present invention relates to the use of ASSNAC and pharmaceutically acceptable salts and solvates thereof in the preparation of a medicament for preventing, alleviating or treating ROS-related oxidative stress caused by an oxidizing agent, increased oxygen exposure, oxygen-induced degeneration or disease, reperfusion injury, ionizing radiation, carcinogenic agents, chemotherapeutic agents, mutagenic agents and laser irradiation damages. In currently preferred embodiments, the use disclosed herein is designated for cells that are part of the central nervous system.

The pathological conditions and diseases to which the compositions of the present invention are directed to are selected from the group consisting of: arthritis (arthritic conditions), atherosclerosis, kidney diseases, cancer, type 2 diabetes, chronic renal insufficiency, chronic obstructive pulmonary disease (COPD), age related macula degeneration (AMD), neurodegenerative diseases including Alzheimer's disease, Parkinson's disease and amyotrophic lateral sclerosis (ALS), and the like.

According to another aspect, the present invention is directed to preventing, alleviating or treating ROS-induced oxidative stress resulting from aging.

According to another aspect, the present invention relates to the use of ASSNAC and pharmaceutically acceptable salts thereof in the preparation of a medicament useful for prolonging the storage life of human or animal cells, tissues or organs in vitro. In one embodiment, the human or animal cells comprise human brain tissue.

According to an additional aspect, the present invention provides a pharmaceutical composition comprising as an active ingredient ASSNAC and pharmaceutically acceptable salts and solvates thereof for up-regulating glutathione levels in cells.

In yet another aspect, the present invention provides a pharmaceutical composition comprising as an active ingredient ASSNAC and pharmaceutically acceptable salts and solvates thereof for preventing, alleviating or treating the effects of oxidative stress induced by reactive oxygen species (ROS). The present invention further provides a pharmaceutical composition comprising as an active ingredient ASSNAC and pharmaceutically acceptable salts and solvates thereof for prolonging the storage life of mammalian cells, tissues, or organs in vitro.

In certain embodiments, the pharmaceutical compositions of the present invention are designated to cells that are part of the central nervous system (CNS). In other embodiments, the pharmaceutical compositions are provided in combination therapy with at least one other active agent. In currently preferred embodiments, the at least one other active agent is pyrrolidine thiocarbamate (PDTC).

The pharmaceutical compositions of the present invention may further include other components selected from, but not limited to, thickeners, carriers, diluents, excipients, surface active agents, and preservatives of the art. Without being bound by any theory or mechanism of action, these components might be added to the compositions to facilitate the stability and/or accessibility of the formulation.

Within the scope of the present invention are the two enantiomeric forms of ASSNAC, derived from either d-cysteine or l-cysteine. Pharmaceutically acceptable salts of ASSNAC according to the present invention may thus comprise counter-ions that contain one or more chiral centers including different diastereomeric pairs or mixtures thereof. It is to be understood that the current invention relates to all the individual enantiomers, diastereomers and respective racemic and non-racemic mixtures thereof. These mixtures of enantiomers and diastereomers can be separated into stereoisomerically uniform components in a known manner or synthesized a priori as separate enantiomers and diastereomers.

In the present specification and claims that follow, co-administration is explicitly meant to include combined therapies that are administered individually or as a single composition. When administered individually, the separate therapeutic agents may be administered at substantially the same time or under a separate regime.

The pharmaceutical compositions of the present invention can be provided in any form known in the art, including, but not limited to, in a form suitable for oral administration (e.g., a solution, a suspension, a syrup, an emulsion, a dispersion, a tablet, a pill, a capsule, a pellet, granules and a powder), in a form suitable for parenteral administration (e.g., intravenous, intramuscular, intra-arterial, transdermal, subcutaneous or intraperitoneal), in a form suitable for topical administration (e.g., an ointment, a gel, a cream), and in a form suitable for administration by inhalation or for administration via suppository.

For use as medicaments for preventing, alleviating or treating an organism in need thereof, the pharmaceutical compositions may be formulated in unit dosage form. The active dose for humans is generally in the range from 0.5 to about 100 mg per kg body weight, in a regimen of 1-5 times a day. However, it is evident to a person skilled in the art that the selected dosage of the active ingredient depends upon the desired therapeutic effect, the route of administration, the duration of the treatment desired, the age of the patient, the weight of the patient, contraindications, co-administration, combination with additional medications and the like.

These and additional benefits and features of the invention could better be understood by those skilled in the art with reference to the following detailed description taken in conjunction with the figures and non-limiting examples.

BRIEF DESCRIPTION OF THE DRAWINGS

The accompanying drawings, which are incorporated in and form a part of the specification, illustrate certain embodiments of the present invention, and together with the description serve to explain the principles of the invention. In the drawings.

DETAILED DESCRIPTION OF THE INVENTION

Figure 1:
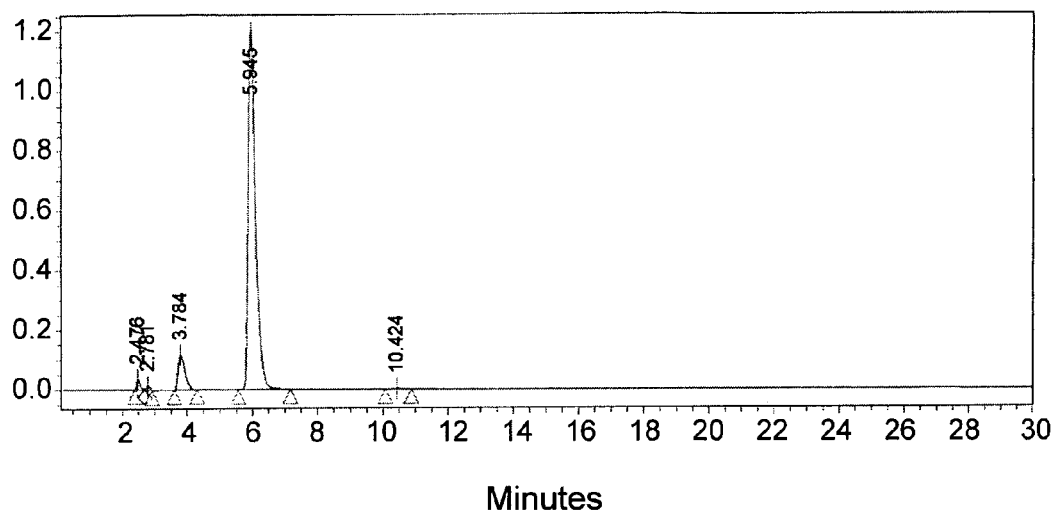
FIG. 1 shows the HPLC analysis of the ASSNAC preparation.

The present invention relates to compositions comprising S-allylmercapto-N-acetylcysteine (ASSNAC) for up-regulating cellular glutathione levels. Methods of use thereof in preventing, alleviating and treating pathological conditions and diseases characterized by increased induction of ROS-related oxidative stress comprising the step of administering an effective amount of a pharmaceutical composition comprising as an active ingredient S-allylmercapto-N-acetylcysteine (ASSNAC) and pharmaceutically acceptable salts and solvates thereof are disclosed as well.

In a first aspect, the present invention provides a method for up-regulating cellular glutathione levels comprising the step of administering an effective amount of a pharmaceutical composition comprising as an active ingredient S-allylmercapto-N-acetylcysteine (ASSNAC) and pharmaceutically acceptable salts and solvates thereof. In one embodiment the up-regulation of cellular glutathione levels is designated to cells that are part of the central nervous system (CNS).

According to another aspect, the present invention relates to the use of ASSNAC and pharmaceutically acceptable salts and solvates thereof according to the present invention in the preparation of a medicament useful for the up-regulation of cellular glutathione levels. In another embodiment, the up-regulation of cellular glutathione levels is designated to cells that are part of the CNS. Other uses within the scope of the present invention are the prevention, alleviation and treatment of oxidative stress induced by ROS.

In addition, the present invention relates to the use of compounds according to the present invention in the preparation of a medicament useful for the prevention, alleviation and treatment of oxidative stress induced by ROS in cells that are part of the CNS.

Oxidative stress induced by ROS is associated with several pathological conditions and diseases including, but not limited to, arthritis, atherosclerosis, type 2 diabetes, cancer and neurodegenerative diseases such as Alzheimer's disease and Parkinson's disease.

The present invention provides methods for preventing, alleviating and treating oxidative stress induced by ROS, particularly in cells that are part of the CNS. The methods disclosed herein comprise administering an effective amount of a pharmaceutical composition comprising as an active ingredient ASSNAC and pharmaceutically acceptable salts and solvates thereof. In some embodiments, the methods for preventing, alleviating and treating ROS-induced oxidative stress are directed to cells that are part of the CNS.

Another embodiment of the present invention relates to a method for the prevention, alleviation and treatment of oxidative stress induced by ROS, comprising the step of administering an effective amount of a pharmaceutical composition comprising as an active ingredient ASSNAC and pharmaceutically acceptable salts and solvates thereof and further comprising co-administering a pharmaceutically effective amount of at least one other pharmaceutically active agent with similar effects towards ROS induced oxidative stress. In certain embodiments, the method for preventing, alleviating and treating ROS-induced oxidative stress is directed to cells that are part of the CNS. A currently preferred embodiment is the co-administering of ASSNAC and pharmaceutically acceptable salts and solvates thereof with a pharmaceutically effective amount of another antioxidant agent, namely PDTC as the second pharmaceutically active agent with similar effects towards ROS-induced oxidative stress.

According to another embodiment, the present invention relates to the use of ASSNAC and pharmaceutically acceptable salts and solvates thereof according to the present invention in the preparation of a medicament useful for the prevention, alleviation or treatment of ROS induced oxidative stress. In particular embodiment, the ROS induced oxidative stress is in cells that are part of the CNS.

According to another aspect, the present invention relates to the use of ASSNAC and pharmaceutically acceptable salts thereof in the preparation of a medicament for prolonging the storage life of human or animal cells, tissues or organs in vitro.

In another embodiment, the invention provides the use of a pharmaceutical composition comprising as an active ingredient ASSNAC and pharmaceutically acceptable salts and solvates thereof for the preparation of a medicament for the prevention, alleviation or treatment of ROS induced oxidative stress, in combination therapy with at least one other active agent with similar effects towards ROS induced oxidative stress. In a currently preferred embodiment, the at least one other active agent with similar effects towards ROS induced oxidative stress is PDTC.

In certain embodiments, the second active ingredient may be administered alongside ASSNAC. The administration can be concurrent (either combined in one dosage form or in separate dosage forms) or sequential. If provided sequentially, ASSNAC can be administered before or after treatment with the second active agent. Preferably, the second active agent is administered after the administration of ASSNAC. Even more preferably, the second active agent to be administered after the administration of ASSNAC is PDTC.

Definitions

To facilitate an understanding of the present invention, a number of terms and phrases are defined hereinbelow. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As used herein, the term "oxidative stress" can be described as "A disturbance in the pro-oxidant/antioxidant balance in favor of the pro-oxidant, leading to potential damage." (Sies et al., in "*Oxidative stress: Oxidants and Antioxidants*", 1991, Academic Press).

As used herein, the term "reactive oxygen species" (ROS) relates to one or a combination of the following:
 a) highly reactive ions wherein the charge is located on the oxygen atom;
 b) free radicals, namely chemical species with a molecular orbital containing a single unpaired electron, wherein the molecular orbital containing the single unpaired electron is located on an oxygen atom;
 c) diradicals, namely a molecular species with two electrons occupying two degenerate molecular orbitals of the same energy;
 d) hydrogen peroxide ($H_2O_2$);
 e) organic hydroperoxides, R—O—O—H, wherein R is an organic group;
 f) organic peroxides, R—O—O—R', wherein R and R' are identical or non-identical organic groups;
 g) Ozone.

Non-limiting examples of reactive oxygen species are superoxide anion, hydroperoxide anion, hydroxyl radical, singlet oxygen, hypochloride anion, tert-Butyl hydroperoxide (($CH_3)_3$C—O—O—H) and the like.

The term "ionizing radiation" refers to energetic particles or waves that contain, individually, enough energy to ionize an atom or molecule. Non-limiting examples of ionizing radiation are energetic beta particles, neutrons, alpha particles, X-rays, gamma rays and photons.

S-allylmercapto-N-acetylcysteine (ASSNAC) exists in two enantiomeric forms derived from either d-cysteine or l-cysteine. Pharmaceutically acceptable salts of ASSNAC may comprise a counter-ion which contains one or more chiral centers so that different diastereomeric pairs or mixtures of such diastereomeric pairs of these salts are possible. It is to be understood that the current invention relates to all the individual enantiomers, diastereomers and respective racemic and non-racemic mixtures thereof. These mixtures of enantiomers and diastereomers can be separated into stereoisomerically uniform components in a known manner or synthesized a priori as separate enantiomers and diastereomers.

"Pharmaceutically acceptable salts" means any salt that is pharmaceutically acceptable and has the desired pharmacological properties. Non-limiting examples are provided in Berge et al. (*J. Pharm. Sci.*, 66, 1, 1977). Such salts, formed for instance by the carboxylic acid group present in ASSNAC include salts that may be derived from an inorganic or organic base, (or an inorganic or organic acid) including amino acids, which is non-toxic and/or bio-acceptable.

Suitable pharmaceutically acceptable base addition salts include, but are not limited to, metallic salts of calcium, lithium, magnesium, potassium, sodium, aluminum and zinc; ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl) amine, phenylethylbenzylamine, dibenzylethylenediamine, procaine, chloroprocaine, quinine, choline, N-methylglucosamine. Salts with amino acids such as glycine, ornithine, histidine, phenylglycine, lysine, and arginine are contemplated. Furthermore, any zwitterionic form of the instant compounds formed by a carboxylic acid and an amino group are contemplated as well.

Pharmaceutically acceptable acid addition salts of the compounds include salts derived from inorganic acids include, but are not limited to, hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids and the like. The salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate or galacturonate (Berge et al., *J. Pharmac. Sci.*, 66, 1, 1977).

The acid addition salts of said basic compounds are prepared by known methods of the art in which the free base form is brought into contact with a sufficient amount of the desired acid to produce the salt. The free base form may be regenerated by contacting the salt form with a base and isolating the free base in the conventional manner. The free base forms may differ from their respective salt forms in certain physical properties such as solubility in polar solvents. For the purposes of the present invention the salts are considered equivalent to their respective free base.

The base addition salts of said acidic compounds are prepared by known methods of the art in which the free acid form is brought into contact with a sufficient amount of the desired base to produce the salt. The free acid form may be regenerated by contacting the salt form with an acid and isolating the free acid in the conventional manner. The free acid forms may differ from their respective salt forms in certain physical properties such as solubility in polar solvents. For the purposes of the present invention the salts are considered equivalent to their respective free acid.

The present invention also includes within its scope solvates of ASSNAC and salts thereof. The term "solvate" as used herein refers to a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. A "hydrate" is a solvate wherein the solvent molecule is water.

The present invention also includes polymorphs of the compounds of the present invention and salts thereof. The term "polymorph" refers to a particular crystalline or amorphous state of a substance, which can be characterized by particular physical properties such as X-ray diffraction, electron diffraction, IR spectra, Raman spectra melting point, and the like.

The "individual" or "patient" for purposes of treatment includes any human or animal affected by any of the diseases where the treatment has beneficial therapeutic impact. Usually, the animal that serves to establish the pre-clinical data and that can be treated by compounds of the invention is a vertebrate such as a primate including chimpanzees, monkeys and macaques, a rodent including mice, rats, ferrets, rabbits and hamsters, a domestic or game animal including bovine species, equine species, pigs, sheep, caprine species, feline species, canine species, avian species, and fishes.

An "organism" comprises the abovementioned "individual" or "patient" and further includes any other living species; animal, plant, fungi, bacteria (eukaryotic and prokaryotic), known or unknown to men.

Pharmaceutical Compositions

The pharmaceutical compositions may contain in addition to the active ingredient or ingredients conventional pharmaceutically acceptable carriers, diluents, excipients, surface active agents, preservatives and the like, all as well known in the art. These components may facilitate the stability and/or bio-acceptability of the formulation. The term "pharmaceutically acceptable" as used herein refers to components which are approved by a regulatory agency of the Federal or a state government or listed in the U.S. Pharmacopeia or other generally recognized pharmacopeia for use in animals and, more particularly, in humans. The terms carrier, diluent or excipient as used herein refer to ingredients that are compatible with the other ingredients of the compositions disclosed herein, especially substances which do not react with the compounds of the invention and are not overly deleterious to the patient or animal to which the formulation is to be administered, thus enabling therapeutically effective and convenient administration of the compounds of the present invention.

In the present specification and claims that follow, co-administration is explicitly meant to include combined therapies that are administered individually or as single composition. When administered individually, the separate therapeutic agents may be administered at substantially the same time or under a separate regime.

The pharmaceutical compositions of the present invention can be formulated for administration by a variety of routes including oral, transdermal, rectal, parenteral (subcutaneous, intraperitoneal, intravenous, intra-arterial, transdermal and intramuscular), topical, intranasal, or via a suppository. Such compositions are prepared in a manner well known in the pharmaceutical art and comprise as an active ingredient at least one compound of the present invention as described hereinabove, and a pharmaceutically acceptable excipient or carrier.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, in a non-limiting example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some non-limiting examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed essentially evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including, but not limited to, a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. Adjuvants for topical or gel base forms may include, for example, sodium carboxymethylcellulose, polyacrylates, polyoxyethylene-polyoxypropylene-block polymers, polyethylene glycol and wood wax alcohols.

Alternative formulations include nasal sprays, liposomal formulations, slow-release formulations, controlled-release formulations and the like, as are known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some preferred embodiments, administration can be by direct injection e.g., via a syringe, at the site of a tumor or neoplastic or pre-neoplastic tissue.

The compositions may also be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

Furthermore, at times, the pharmaceutical compositions may be formulated for parenteral administration (subcutaneous, intravenous, intra-arterial, transdermal, intraperitoneal or intramuscular injection) and may include aqueous and non-aqueous, isotonic sterile injection solutions, which can contain preservatives, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Prior to their use as medicaments for preventing, alleviating or treating an organism in need thereof, the pharmaceutical compositions may be formulated in unit dosage form. The active dose for humans is generally in the range from 0.5 to about 100 mg per kg body weight, in a regimen of 1-5 times a day. However, it is evident to a person skilled in the art that the dosage of the active ingredient will be determined by the attending physician and depends upon the desired therapeutic effect, the route of administration, the duration of the treatment desired, the age of the patient, the gender of the patient, the weight of the patient, contraindications, co-administration and combination with additional medications and the like.

Pharmaceutical compositions of the present invention may also include one or more additional active ingredients. When two or more active ingredients are administered to achieve the therapeutic goals of the present invention, co-administration can be in a unique dosage form or in separate dosage forms for combined administration. Combined administration in the context of this invention is defined to mean the administration of more than one therapeutic in the course of a coordinated treatment to achieve an improved clinical outcome. Such combined administration may occur at the same time and also be coextensive, that is, occurring during overlapping periods of time.

As used herein, the "pharmaceutically effective amount" indicates that active compounds achieve the targeted biological activity following the administration of the desired dosage in a reasonable volume.

The term "chemotherapeutic agent" refers to any chemical agent that is used for the alleviation or treatment of cancer.

The term "cancer" in the context of the present invention includes all types of neoplasm whether in the form of solid or non-solid tumors, and includes both malignant and premalignant conditions as well as their metastasis.

The term "carcinogenic agents" refers to any substance, radionuclide or radiation which is directly involved in the promotion of cancer or in the facilitation of its propagation.

The term "mutagenic agent" in the context of the present invention refers to agents such as chemical compounds, ultraviolet light, or radioactive elements that can induce or increase the frequency of mutation in an organism.

The term "reperfusion injury" refers to damage to tissue caused when blood supply returns to the tissue after a period of ischemia.

The term "aging" as used herein generally refers to any damage to the cells caused by toxic byproducts of oxygen metabolism. Such aging can, for example, result from partial damage or complete destruction of cells or from the conversion of imide bonds to amide bonds in proteins resulting in hardening of the arteries or skin wrinkling, etc. Thus, the phrase "preventing, alleviating or treating ROS-induced oxidative stress resulting from aging" means preventing, alleviating or treating any damage to cells caused by ROS-induced oxidative stress.

The term "central nervous system" (CNS) refers to the part of the nervous system that includes the brain and the spinal cord.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials

Sodium thiosulfate pentahydrate was purchased from Fluka. Allyl bromide was purchased from Aldrich. NAC and PDTC were purchased from Sigma. CSSA was prepared as described in Rabinkov et al. (*Biochim. et Biophys. Acta*, 1379, 233, 1998).

Materials for the Preparation of ASSNAC:

Sodium thiosulfate anhydrous (Gadot); Allyl bromide (Acros); and L-N-Acetylcystein (NAC) from Sigma (A9165).

Preparation of ASSNAC:

Step 1: Preparation of Allyithiosulfate

An amount of 310 grams of sodium thiosulfate (1.98 mole) were dissolved in water to a final volume of 990 ml. The solution was cooled in an ice bate. Cold Allyl bromide (171 ml; 1.98 mole) was added (initially it is a two phase mixture). The mixture was stirred in a cold room over night until it became homogeneous and slightly turbid.

Step 2: Preparation of ASSNAC

NAC (64.8 gram; 0.397 mole) was dissolved in 794 ml of phosphate buffer (0.5M; pH 8: 106.4gr $Na_2HPO_4.7H_2O$), cooled to 0° C. following by the addition of a cold solution of allylthiosulfate (990 ml, prepared in step 1), stirring at 0° C. and bubbling with $N_2$ for 48 hours. The composition of the solution according to HPLC analysis is: ASSNAC 33.9% and NAC 59.3%. Following 110 hours of incubation (0° C.; no stirring) phase separation has occurred and the upper organic layer was removed. The remaining aqueous phase, according to the HPLC analysis, contained: ASSNAC 19% and NAC 73%.

Step 3: Purification of ASSNAC

The mixture obtained in step 2 was extracted with t-Buthyl methyl ether (MTBE), twice with an equal volume and once with half the volume of the aqueous phase. The combined organic phases (MTBE) were evaporated under vacuum. The resulting yellowish oil crystallized after a while.

Analysis:

$^1H$ NMR ($d_6$-acetone): 2.9 (m, 2H), 3.38 (d, 2H allyl), 4.72 (m, 1H), 5.15 (m, 2H allyl), 5.80 (m, 1H allyl);

FIG. 1 shows the HPLC analysis (C-18; $\lambda$=205 nm, 30% acetonitrile-69% water-1% Acetic acid, flow 1 ml/min) of purified ASSNAC. The ASSNAC appears at a retention time (RT) of 5.94 minutes, and the NAC appears at a retention time of 3.78 minutes. The purity of the preparation is 91.8%.

Cell Culture

Bovine aortic endothelial cells (EC) were prepared from bovine aorta, cultured in DMEM supplemented with 5% fetal calf serum, 5% calf serum, 2 mM L-glutamine, 100 U/ml penicillin, 100 μg/ml streptomycin, 12.5 U/ml nystatin and FGF-2 (3 ng/ml; added every 48 hours). Cultures were incubated at 37° C. in a humidified 10% $CO_2$ atmosphere and passages 12-18 were used for experiments.

In order to establish the potential effect of ASSNAC on glutathione up-regulation in the nerve system as a mean to protect against neurodegenerative diseases the effect of ASSNAC on the human neuroblastomas SH-SY5Y cell line was studied. The cells were cultured in DMEM supplemented with 10% fetal calf serum, 2 mM L-glutamine, 100 U/ml penicillin, 100 μg/ml streptomycin, 12.5 U/ml nystatin. Cultures were incubated at 37° C. in a humidified 10% $CO_2$ atmosphere.

Determination of Total Glutathione

EC cultures were incubated in the presence or absence of PDTC, NAC, ASSNAC and their combinations. At the end of the incubation, cells were washed, collected into 10 mM HCl and further lyzed by samples freezing (in liquid nitrogen) and thawing, 3 times. Cell protein was precipitated by addition of SSA (10%) followed by centrifugation at 10,000 g and supernatant was collected for glutathione determination. Total glutathione (GSH+GSSG) was determined by the Anderson recycling method. Briefly, a reaction mixture containing phosphate buffer, EDTA, DTNB, NADPH and glutathione reductase was added to 96-wells plates already containing 20 μl of the experimental samples or a GSSG standard. The plates were shaken and OD at 405 nm was monitored at 10 sec intervals for 130 sec in a micro-plate reader. To determine the GSSG level in the total cellular glutathione, 2-vinylpyridine was used to conjugate GSH and remove it from the mixture followed by total glutathione determination as described above. For normalization, the protein pellet of each sample was lyzed in 0.2 N NaOH and quantified by the Lowry method.

Cytotoxicity Test

Endothelial cells (EC; $10^4$ cells/well) were grown till confluency in fibronectin-coated (5 µg/ml) 96 wells plates. Confluent EC were pre-incubated with ASSNAC 0.2 mM, CSSA 0.2 mM and NAC 1 mM for 18 hours in growth medium at 37° C. Subsequently, cells were washed with serum free DMEM medium and treated with BuOOH (tert-butylhydroperoxide) 0.1 mM for 3 hours. The number of viable cells was determined by Neutral Red (NR) staining method. After removing the culture medium, cells were incubated in NR working solution (1:100 in DCCM) for 2 hours at 37° C. Wells were washed twice with PBS to remove unincorporated dye and the dye was extracted with Sorrenson solution (0.07M Trisodium Citrate, 0.03M Citric acid and 0.1N HCl) at room temperature. Optical density of the dye was determined at 550 nm in an ELISA reader. The cell cytotoxicity was calculated by the following formula: Cytotoxicity (%)=[1−NR uptake in treated wells/NR uptake in control wells]×100 The control (untreated wells) were determined as 0% cytotoxity, the average of triplicates of each treatment is shown.

Determination of Gene Expression by Real-Time PCR

Total RNA was collected by EZ-RNA 2 kit, treated with DNAse, converted to cDNA and assayed in triplicate by real-time quantitative PCR using a ABI Prism 7700 Sequence Detector System (Applied Biosystem, Foster City, Calif., USA), with Absolute SYBR Green ROX mix and analyzed (SDS 2.1 software). Primers: human glutamate-cysteine-ligase modifier subunit (GCLM)—Forward: 5'GGCACAGG-TAAAACCAAATA GTAAC3'
and Reverse: 5'CAAATTGTTTAGCAAATGCAGTCA3';
Human heme oxygenase-1 (HO-1)—Forward: 5'TTCTC-CGATGGGTCCTTACACT3'
and Reverse: 5'GGCATAAAGCCCTACAGCAACT3';
bovine TGF β2—Forward: CTAAAGGGTACAATGC-CAACTTCTGT
and Reverse: GAGAATGGTGAGCGGCTCTAAAT;
bovine TNF-alfa—Forward: CATCCTGTCTGCCAT-CAAGA
and Reverse: GGCGATGATCCCAAAGTAGA;
bovine ICAM-1—Forward: CCATGGCAC-CAATTTCTCTT
and Reverse: GTCTGAGGCTGGGAACAGTC;
bovine VCAM-1 Forward: GAACCGACAGCTCCTTTCTG
and Reverse: TCCCTGACATCACAGGTCAA.
Results were normalized based on the quantity of human β-actin. Primers—Forward: 5'CCTGGCACCCAGCA-CAAT3' and Reverse: 5'GCCGATCCACACGGAG-TACT3'.

Example 1

Glutathione Level in Response to ASSNAC and CSSA as a Function of Time

Figure 2A:
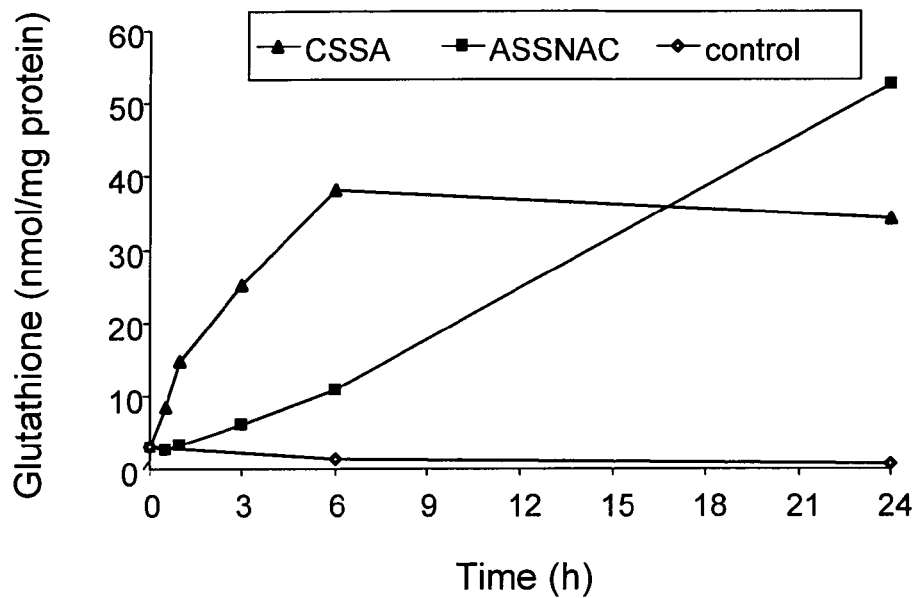
FIG. 2A shows the time-response of the glutathione level in the presence of ASSNAC and CSSA vs. control in endothelial cells.

Exposure of endothelial cells (EC) to ASSNAC and CSSA both at a concentration of 0.2 mM resulted in a significant increase in glutathione cellular level as a function of time. Though the CSSA induced a faster response, after 24 hours a higher glutathione level was observed with ASSNAC in comparison to CSSA (FIG. 2A).

Example 2

Glutathione Level in Response to ASSNAC—Concentration Titration Curve

Figure 2B:
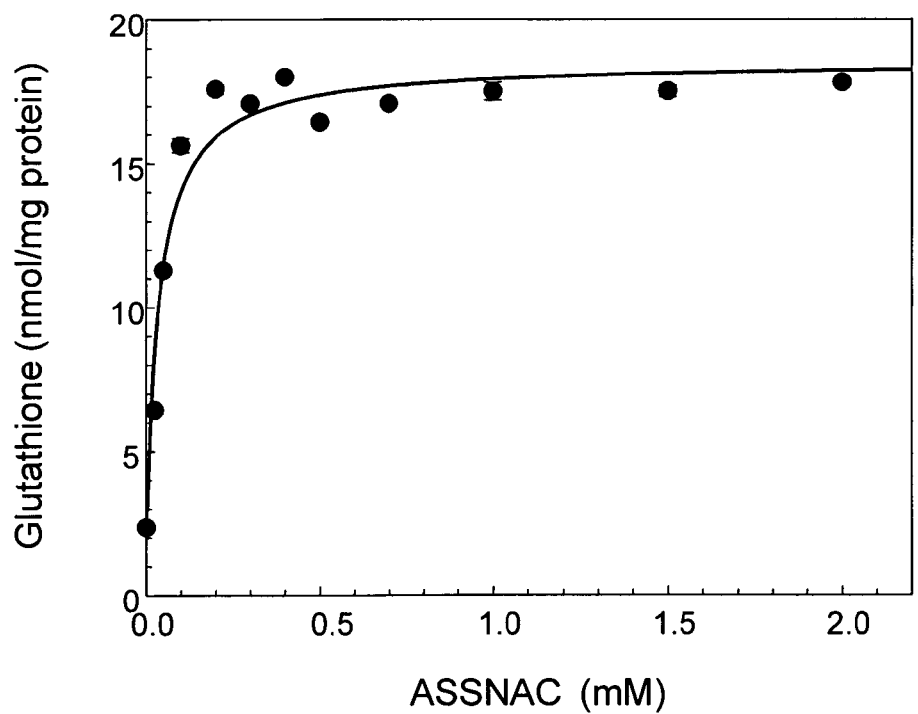
FIG. 2B shows the glutathione level in response to ASSNAC—concentration titration curve in endothelial cells.

Exposure of endothelial cells (EC) to ASSNAC for 24 hours at increasing concentrations resulted in significant dose dependent up-regulation of glutathione level starting at a concentration of 0.05 mM reaching maximal effect at 0.2 mM that was maintained up to a concentration of 2.0 mM without any signs of cytotoxic effect (FIG. 2B).

Example 3

Glutathione Level in Response to NAC—Concentration and Time Titration Curves

A. Concentration Titration Curve

Figure 3A:
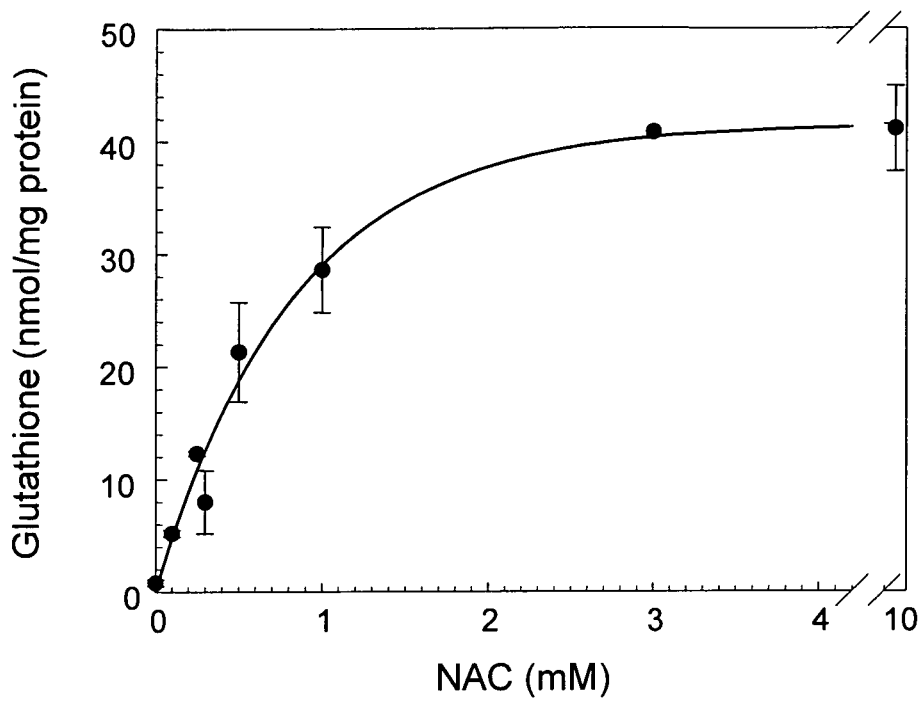
FIG. 3A shows the glutathione level in response to NAC—concentration titration curve in endothelial cells.

Exposure of endothelial cells to NAC for 24 hours at increasing concentrations resulted in a significant dose-dependent increase in glutathione level reaching maximal increase at a concentration of 2 mM NAC (FIG. 3A).

B. Time Titration Curve

Figure 3B:
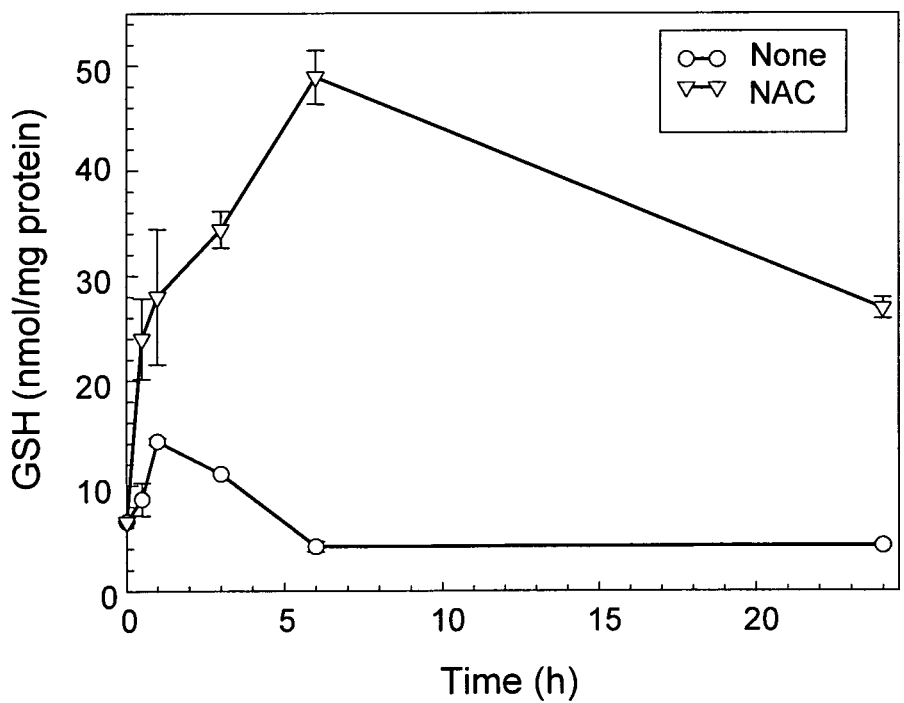
FIG. 3B shows a time dependent increase in the glutathione level induced by the exposure of endothelial cells to NAC for various time periods.

Exposure of endothelial cells to NAC (2 mM) for various time intervals resulted in a time dependent increase in glutathione level reaching maximal increase after 6 hours (FIG. 3B).

Thus, table 1 summarizes the half-maximal and maximal effects of increased glutathione level by NACSSA, CSSA, NAC and allicin observed for varying concentrations.

TABLE 1

The effects of increased glutathione level by NACSSA, CSSA, NAC and allicin.

|  | HALF-maximal | Maximal effect | Maximal Fold Increase |
| --- | --- | --- | --- |
| NACSSA | 60 µM | 200 µM | 4 |
| CSSA | 70 µM | 200 µM | 2 |
| NAC | 320 µM | 500 µM | 2.5 |
| Allicin* | 7 µM | 20 µM | 8 |

(*L. Horev-Azaria, Ph.D. Thesis, Tel Aviv University)

Example 4

Figure 4:
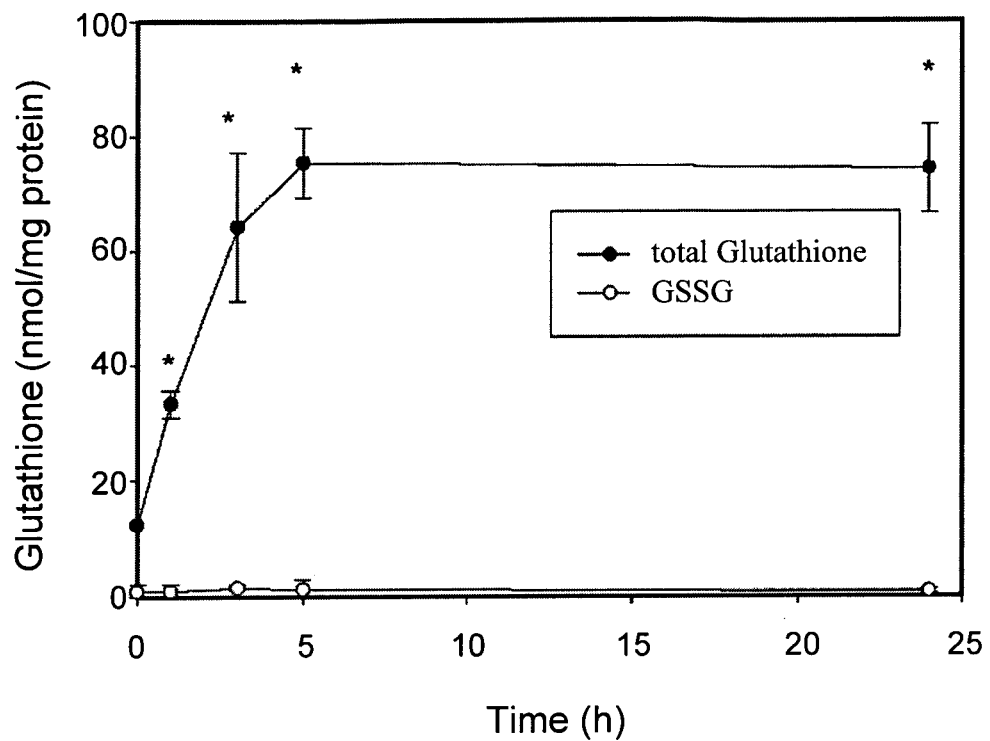
FIG. 4 shows the amount of total glutathione and oxidized glutathione (GSSG) in allicin derivative (CSSA) treated endothelial cells as a function of time. * represents a significant difference from the control at $p<0.05$.

CSSA Induced Cellular Glutathione in Endothelial Cells—Distribution Between Reduced and Oxidized Glutathione The glutathione values presented herein represent total cellular glutathione, namely GSH plus oxidized glutathione (GSSG). In order to determine the effect of CSSA on the amount of GSSG of the total glutathione level, confluent endothelial cells (EC) were incubated with 0.3 mM CSSA for different time intervals. After incubation, the level of total glutathione and GSSG level was determined and presented as mean±SD of two independent experiments performed in duplicate (FIG. 4). Glutathione up-regulation reflected an increase in GSH but not in GSSG level. Furthermore, the GSSG level in either resting (time point 0) or CSSA-treated EC was lower than 2% of the total cellular glutathione level. These results indicate that the increase in total glutathione reflects an increase in the antioxidant capacity of the cells.

Example 5

The Effect of ASSNAC on BuOOH-Stimulated Cytotoxicity in Endothelial Cells (EC)

Figure 5:
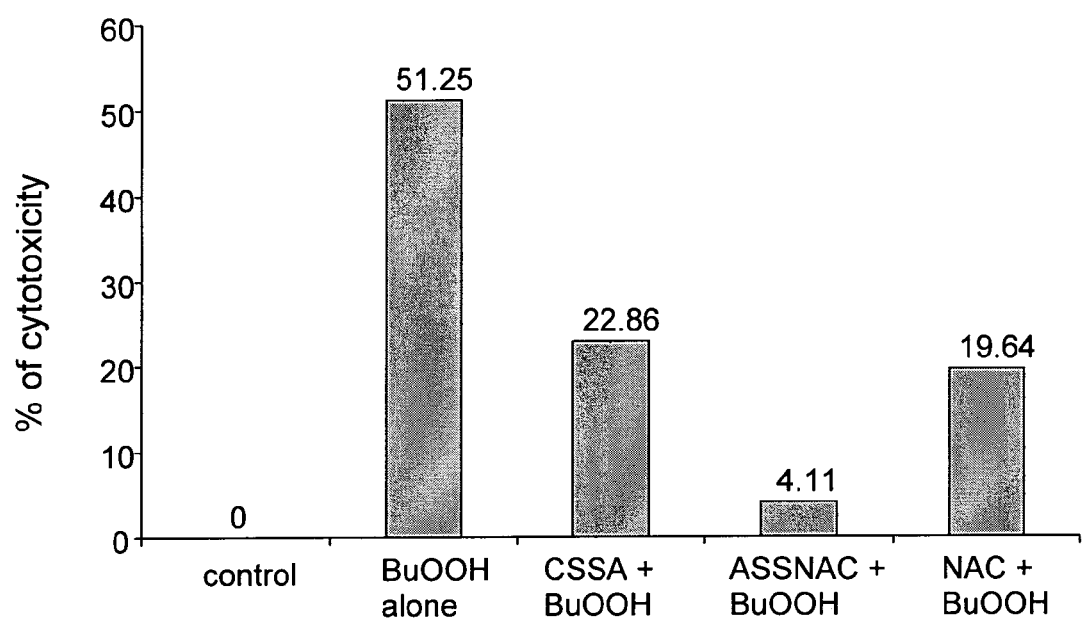
FIG. 5 shows the effect of ASSNAC, CSSA and NAC on BuOOH-stimulated cytotoxicity in endothelial cells.

The effect of pre-incubation (18 hours) with NAC (1 mM), CSSA (0.2 mM) and ASSNAC (0.2 mM) on the cytotoxic effect of BuOOH in endothelial cells was studied. ASSNAC produced better protection of cells from the oxidation stress in comparison to NAC and CSSA (FIG. 5).

Example 6

The Effect of NAC and ASSNAC on Gene Expression in Endothelial Cells (EC)

Increased expression of the phase II detoxifying enzymes by cells is indicative of increased protection against oxidative stress. In order to determine the effect of NAC and ASSNAC on gene expression in EC, cells were treated with NAC (2 mM) and ASSNAC (0.2 mM) for 3 hours following by extraction of mRNA. The expression of GCLM and HO-1 was then studied by Real-Time PCR. The supply of cystein, the substrate in glutathione synthesis, to cells was shown to be NAC-dependent. Without being bound by any theory or mechanism of action, the GCLM activity and the cystein level are considered to be the rate limiting step of the glutathione synthesis. However, NAC did not induce the expression of the phase II detoxifying enzymes. In contrast, ASSNAC induced the expression of both GCLM and HO-1 that are part of the phase II detoxifying enzymes (Table 2A). Thus, without being bound by theory ASSNAC may up-regulates glutathione level by its dual activity—supply of cystein and up-regulation of GCLM expression. Furthermore, ASSNAC induces the expression of HO-1 that is part of the phase II detoxifying enzymes protecting cells from ROS activity.

The effect of ASSNAC on gene expression was further shown to be specific. Endothelial cells (EC) were treated by ASSNAC (0.2 mM) and LPS (1 µg/ml) for 3 hours following by mRNA extraction. The expression of the inflammatory genes TGF β2, ICAM-1, VCAM-1 and TNFα was then studied by Real-Time PCR. The ASSNAC effect did not include inflammatory genes such as ICAM-1 and VCAM-1 that are induced by LPS. Only TGF β2 was induced by ASSNAC and to a lesser extent by LPS. TNFα expression was not induced by either ASSNAC or LPS (Table 2B).

TABLE 2A

The effect of NAC and ASSNAC on gene expression in EC.

| Phase II detoxifying enzymes | NAC 3 hours | ASSNAC 3 hours |
|---|---|---|
| GCLM | $1.0 \pm 0.2$ (n = 3) | $2.3 \pm 1.0$ (n = 4) |
| HO-1 | $0.9 \pm 0.1$ (n = 3) | $8.2 \pm 4.2$ (n = 4) |

TABLE 2B

The effect of ASSNAC and lipopolysacharide (LPS) on gene expression in EC.

| Inflammatory genes | ASSNAC 3 hours | LPS 3 hours |
|---|---|---|
| TGF β2 | 2.14 | 5.7 |
| ICAM-1 | 1.03 | 19.52 |
| VCAM-1 | 0.94 | 104.7 |
| TNFα | 0.77 | 0.71 |

Example 7

Effect of Pyrrolidine Dithiocarbamate (PDTC) on the Glutathione Level in Endothelial Cells (EC)

Figure 6A:
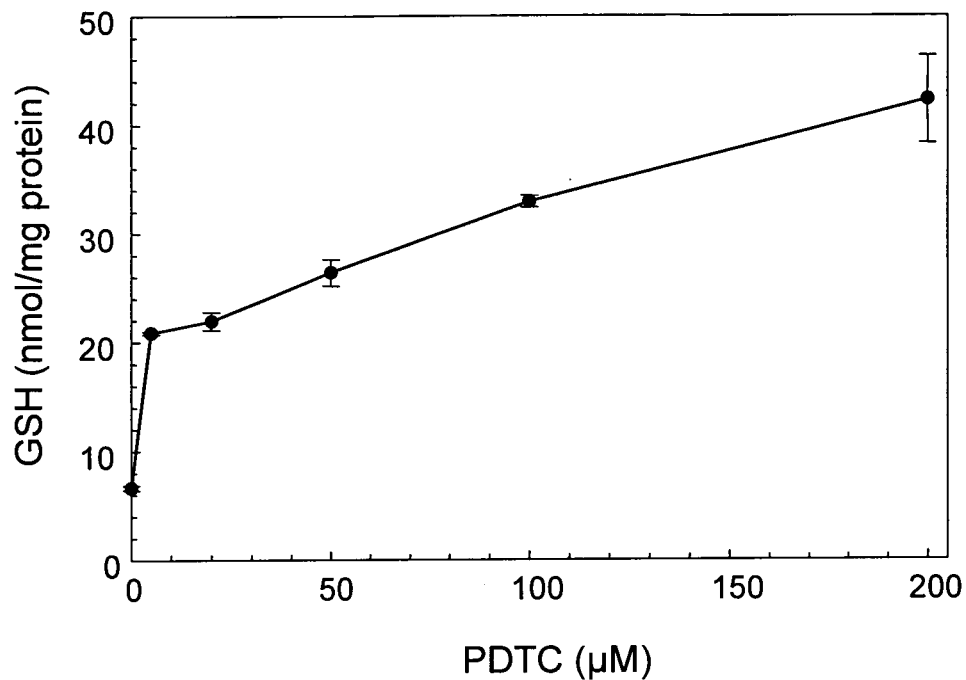
FIG. 6A shows the concentration of reduced glutathione (GSH) in endothelial cells as a function of PDTC concentration after 24 hours exposure.

Incubation of EC for 24 hours with increasing concentrations of PDTC resulted in a concentration dependent increase of reduced glutathione (GSH; nmol/mg protein) (FIG. 6A).

Figure 6B:
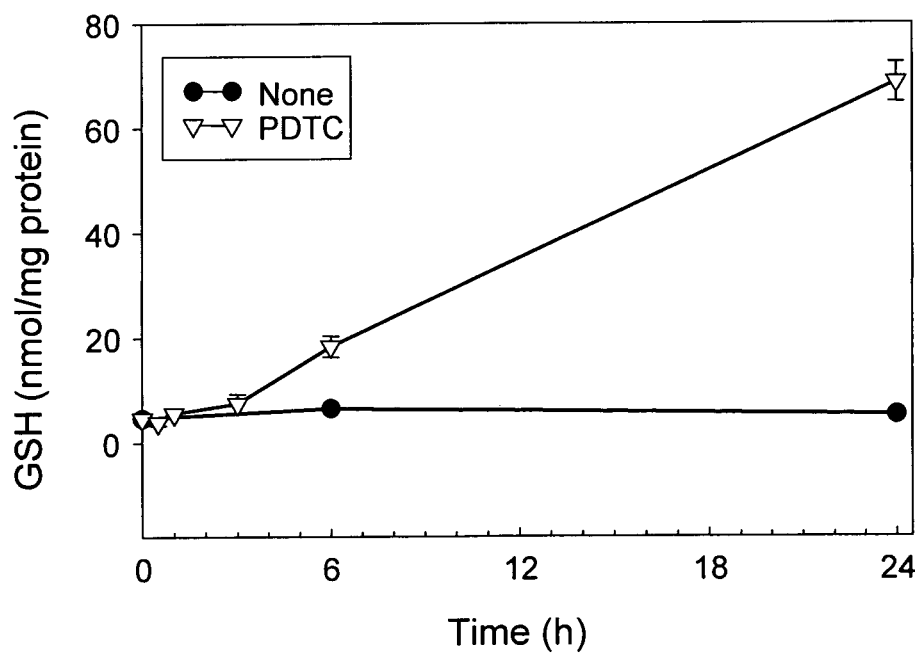
FIG. 6B shows the concentration of GSH in endothelial cells as a function of time at a PDTC concentration of 0.1 mM.

Incubation of EC with PDTC (0.1 mM) for increasing time intervals resulted in a linear increase in the concentration of GSH (nmol/mg protein) during the entire experimental period (FIG. 6B).

Example 8

The Combined Effect of Pyrrolidine Dithiocarbamate (PDTC) and ASSNAC on the Glutathione Level in Endothelial Cells (EC)

Endothelial cells were incubated with the following reagents: (i) NAC (1 mM) for 6 hours; (ii) PDTC (0.1 mM) for 24 hours; (iii) ASSNAC (0.2 mM) for 24 hours; (iv) combination of PDTC (0.1 mM) for 24 hours and NAC (1 mM) for the last 6 hours of incubation; and (v) combination of PDTC (0.1 mM) and ASSNAC (0.2 mM) for 24 hours (FIG. 7).

Without being bound by any theory or mechanism of action, the up-regulation of glutathione biosynthesis is PDTC-dependent through a mechanism similar to allicin (probably by up-regulating the level of the rate limiting enzyme in glutathione biosynthesis). NAC, however, provides a glutathione precursor. Hence, the potential additive effect of both molecules was tested. The ability of ASSNAC to serve as a source of cellular glutathione precursor reservoir as well as an inducer of glutathione biosynthesis was further tested. The reagents were used at their optimal concentration and exposure time. The cultures were then washed and the cellular level of total glutathione was determined.

Figure 7:
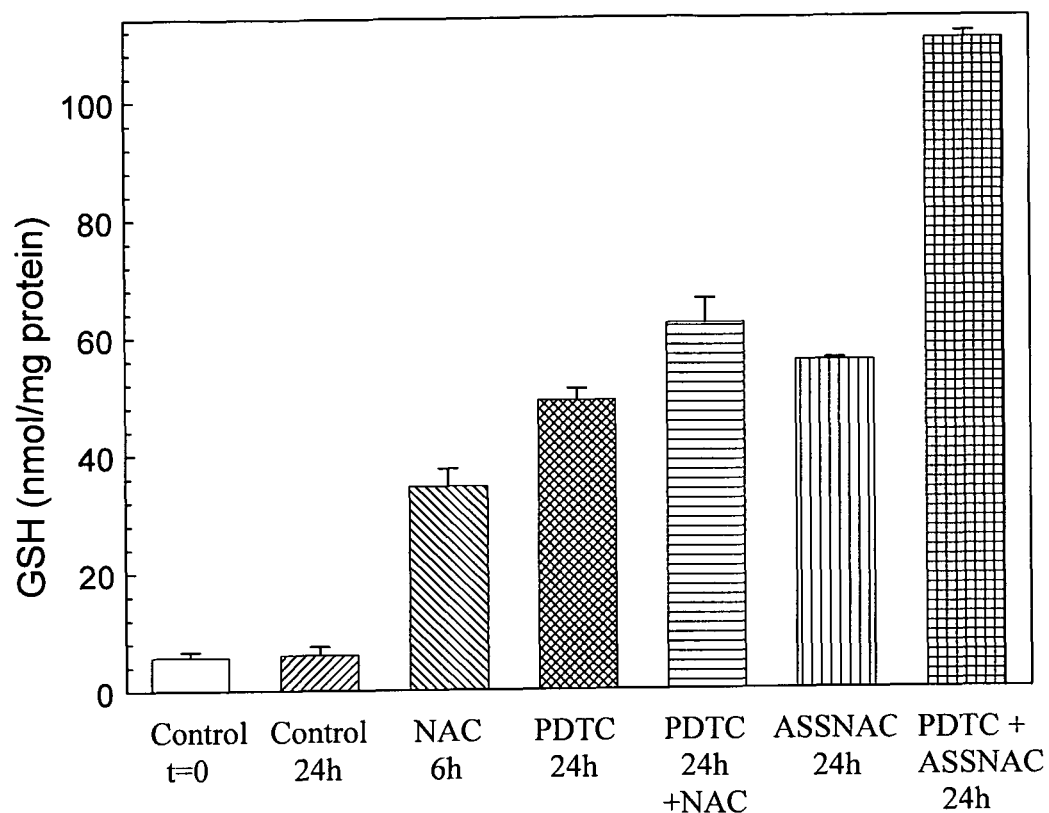
FIG. 7 shows the additive effect of PDTC in combination with NAC and ASSNAC in the up-regulation of GSH in endothelial cells.

FIG. 7 clearly shows that the addition of NAC on top of PDTC results in a slight increase in glutathione level, while the addition of ASSNAC on top of PDTC results in a complete additive effect demonstrating a significant increase in glutathione level.

Example 9

The effect of ASSNAC in human neuroblastoma SH-SY5Y cells

The effect of ASSNAC on glutathione level in EC presented herein, suggests the potential use of ASSNAC in the attenuation of atherosclerosis progression and may further suggest a similar effect in other tissues. In order to establish the potential effect of ASSNAC on glutathione up-regulation in the nerve system as a mean to protect against neurodegenerative diseases, the effect of ASSNAC on the human neuroblastomas SH-SY5Y cell line was studied.

Figure 8A:
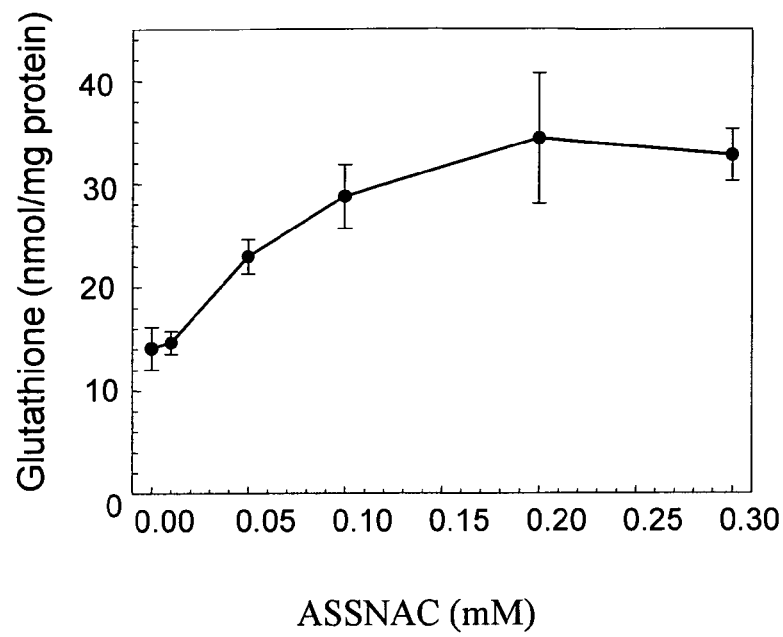
FIG. 8A shows a dose dependent up-regulation of glutathione cellular level in SH-SY5Y cell line by ASSNAC.

Incubation of SH-SY5Y cultures with increasing concentrations of ASSNAC for 24 hours resulted in a dose dependent increase in the cellular level of glutathione. The effect was observable at a concentration of 0.05 mM with a 2.4-fold maximal increase in glutathione at a concentration of 0.2 mM. The results are presented as mean±SD (n=2). A significant increase in glutathione was determined by ANOVA analysis ($p<0.005$; FIG. 8A).

Figure 8B:
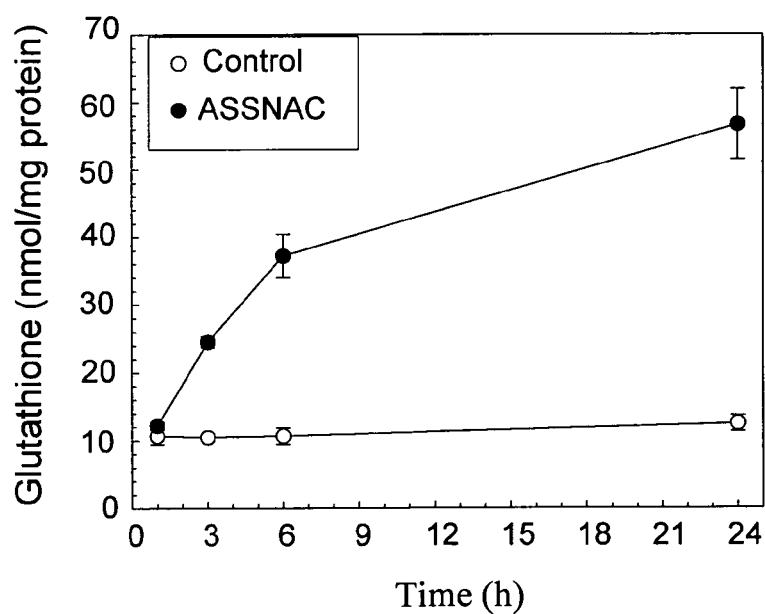
FIG. 8B shows up-regulation of glutathione cellular level in SH-SY5Y cell line by ASSNAC—a time titration curve.

Confluent SH-SY5Y cultures were exposed to ASSNAC (0.2 mM) for various time periods. The cultures were then washed and the cellular level of total glutathione was determined. Cultures exposed to ASSNAC (0.2 mM) demonstrated a time dependent linear increase in glutathione wherein a maximal increase was observed after 24 hours. The results are presented as mean±SD (n=2). A significant increase in glutathione was determined by ANOVA analysis ($p<0.005$; FIG. 8B).

Figure 9:
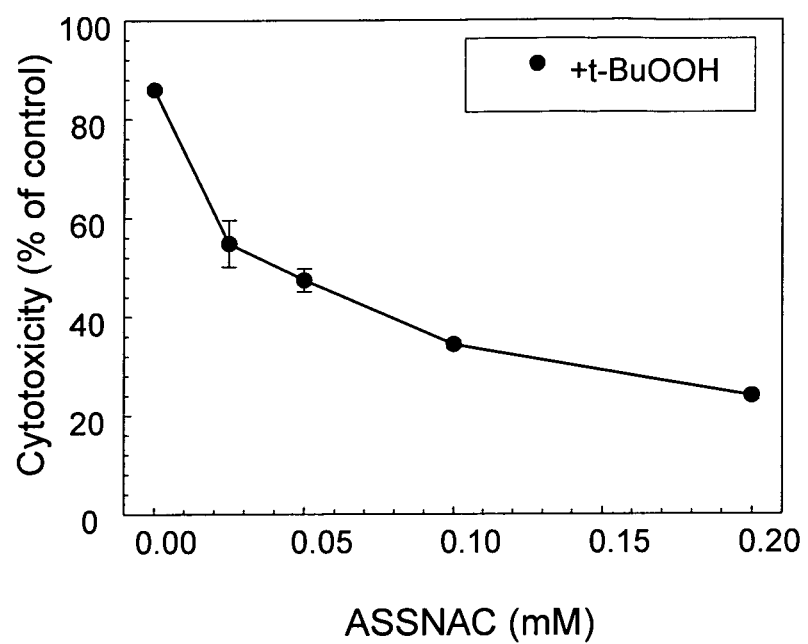
FIG. 9 shows the protective role of ASSNAC against the cytotoxicity effect of tBuOOH in SH-SY5Y cell line—a dose response curve.

The capacity of the ASSNAC pretreatment of SH-SY5Y cultures to protect the cells from oxidative stress is presented in FIG. 9. Confluent SH-SY5Y cultures were exposed to ASSNAC (0.2 mM) for 24 hours and then exposed to tBuOOH (1 mM) for 3 hours. The amount of live cells attached to the tissue culture well at the end of the treatment was determined by the neutral red staining. The results are presented as % cytotoxicity (% difference in amount of stain between tBuOOH untreated and treated cultures). The results are presented as mean±SD (n=2). A significant decrease in cytotoxicity was determined by ANOVA analysis (p<0.001).

The exposure of cells to tBuOOH resulted in 85% cytotoxicity and pretreatment with ASSNAC demonstrated a concentration dependent decrease in the cytotoxicity starting from a concentration of 0.025 mM reaching almost complete protection of the cells at a concentration of 0.2 mM with a cytotoxicity as low as 25%. ASSNAC is thus shown to protect SH-SY5Y cultures from oxidative stress.

While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of attenuating, alleviating or treating the effects of oxidative stress induced by reactive oxygen species (ROS) in an individual in need thereof, comprising administering an effective amount of a pharmaceutical composition comprising as an active ingredient S-allylmercapto-N-acetylcysteine (ASSNAC), and pharmaceutically acceptable salts or solvates thereof, wherein the oxidative stress is formed by a condition selected from the group consisting of aging, arthritis, cancer, atherosclerosis, kidney diseases, type 2 diabetes, chronic obstructive pulmonary disease (COPD), age related macula degeneration (AMD), neurodegenerative diseases, Alzheimer's disease, Parkinson's disease, and amyotrophic lateral sclerosis (ALS).

2. The method of claim 1, wherein the reactive oxygen species are formed by at least one of an oxidizing agent, increased oxygen exposure, oxygen-induced degeneration, oxygen-induced disease, reperfusion injury, ionizing radiation, carcinogenic agents, chemotherapeutic agents, mutagenic agents, and laser irradiation damages.

3. The method of claim 1, wherein the individual is a human.

4. The method of claim 1, wherein the pharmaceutical composition further comprises a pharmaceutically acceptable carrier, diluent or excipient.

5. The method of claim 1, wherein the active ingredient ASSNAC and pharmaceutically acceptable salts or solvates thereof are administered in a daily dose of about 0.5 to about 100 mg per kg body weight.

6. The method of claim 1, wherein the pharmaceutical composition is administered in the form selected from the group consisting of tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders.

7. The method of claim 1, wherein the pharmaceutical composition is administered via a route selected from the group consisting of oral, subcutaneous, intraperitoneal, rectal, intravenous, intra-arterial, transdermal, intramuscular, topical, and intranasal.

8. The method of claim 1, further comprising co-administering ASSNAC with at least one other active agent.

9. The method of claim 8, wherein the at least one other active agent is pyrrolidine thiocarbamate (PDTC).

10. The method of claim 8, wherein co-administration of the therapeutic agents is performed in a regimen selected from: a single combined composition; separate individual compositions administered substantially at the same time; and separate individual compositions administered under separate schedules.

11. The method of claim 1, wherein the treatment comprises up-regulating of glutathione levels in cells.

12. The method of claim 11, wherein the cells are part of the central nervous system.

13. A method of attenuating, alleviating or treating the effects of oxidative stress induced by reactive oxygen species (ROS) in an individual suffering from a pathological central nervous system condition, comprising administering an effective amount of a pharmaceutical composition comprising as an active ingredient S-allylmercapto-N-acetylcysteine (ASSNAC), and pharmaceutically acceptable salts or solvates thereof.

14. The method of claim 13, wherein the individual is a human.

15. The method of claim 13, wherein the pharmaceutical composition further comprises a pharmaceutically acceptable carrier, diluent or excipient.

16. The method of claim 13, wherein the active ingredient ASSNAC and pharmaceutically acceptable salts or solvates thereof are administered in a daily dose of about 0.5 to about 100 mg per kg body weight.

17. The method of claim 13, wherein the pharmaceutical composition is administered in the form selected from the group consisting of tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders.

18. The method of claim 13, wherein the pharmaceutical composition is administered via a route selected from the group consisting of oral, subcutaneous, intraperitoneal, rectal, intravenous, intra-arterial, transdermal, intramuscular, topical, and intranasal.

19. The method of claim 13, further comprising co-administering ASSNAC with at least one other active agent.

20. The method of claim 19, wherein the at least one other active agent is pyrrolidine thiocarbamate (PDTC).

21. The method of claim 19, wherein co-administration of the therapeutic agents is performed in a regimen selected from: a single combined composition; separate individual compositions administered substantially at the same time; and separate individual compositions administered under separate schedules.

22. A method of attenuating, alleviating or treating the effects of oxidative stress induced by reactive oxygen species (ROS) in an individual in need thereof, comprising administering an effective amount of a pharmaceutical composition comprising as an active ingredient S-allylmercapto-N-acetylcysteine (ASSNAC), and pharmaceutically acceptable salts or solvates thereof, wherein the oxidative stress is formed by a condition selected from the group consisting of atherosclerosis, type 2 diabetes, age related macula degeneration (AMD) and Alzheimer's disease.

23. The method of claim 22, further comprising co-administering ASSNAC with at least one other active agent.

24. The method of claim 23, wherein the at least one other active agent is pyrrolidine thiocarbamate (PDTC).

25. The method of claim 23, wherein co-administration of the therapeutic agents is performed in a regimen selected from: a single combined composition; separate individual compositions administered substantially at the same time; and separate individual compositions administered under separate schedules.

\* \* \* \* \*